United States Patent [19]
Braxton et al.

[11] Patent Number: 5,856,109
[45] Date of Patent: Jan. 5, 1999

[54] HOMOLOG OF RAT ELASTASE IV DERIVED FROM HUMAN PANCREAS

[75] Inventors: Scott M. Braxton, San Mateo; Dinh Diep, San Francisco; Angelo M. Delegeane, Milpitas, all of Calif.

[73] Assignee: Incyte Pharmaceuticals, Inc., Palo Alto, Calif.

[21] Appl. No.: 966,319

[22] Filed: Nov. 7, 1997

Related U.S. Application Data

[62] Division of Ser. No. 568,031, Dec. 6, 1995.
[51] Int. Cl.[6] .............................. G01N 33/53; C07K 1/00
[52] U.S. Cl. ............................................. 435/7.6; 530/350
[58] Field of Search .............................. 530/350; 435/7.6

[56] References Cited

FOREIGN PATENT DOCUMENTS

WO 96/01270   1/1996   WIPO .

OTHER PUBLICATIONS

Edwards, P.D. et al., "Synthetic Inhibitors of Elastase", *Med. Res. Rev.*, Mar. 1994, 142(2), pp. 127–194—Abstract Only.

Gross, V. et al., "Inflammatory Mediators and Cytokins—New Aspects of the Pathophysiology and Assessment of Severity of Acute Pancreatitis?", *Hepatogastroenterology*, Dec. 1993, 40(6), pp. 522–530—Abstract Only.

Kang, J. et al., "Identification of cDNSs Encoding Two Novel Rat Pancreatic Serine Proteases", Gene, 110 (2), 181–187 (1992) Abstract Only (EMBL accession X59014).

Ngo, J.T. et al., "Computational Complexity, Protein Structure Prediction, and the Levinthal Paradox", *The Protein Folding Problem and Tertiary Structure Prediction*, 1994, pp. 433–440.

Gewirtz, A.M. et al., "Facilitating oligonucleotide delivery: Helping antisense deliver on its promise", *Proc. Natl. Acad. Sci. USA*, Apr. 1996, 93, pp. 3161–3163.

James, W., "Towards gene–inhibition therapy: a review of progress and prospects in the field of antiviral antisense nucleic acids and ribozymes", *Antiviral Chemistry & Chemotherapy*, 1991, 2(4), pp. 191–214.

*Primary Examiner*—Nancy Degen
*Assistant Examiner*—Andrew Wang
*Attorney, Agent, or Firm*—Lucy J. Billings; Incyte Pharmaceuticals, Inc.

[57] ABSTRACT

The present invention provides nucleotide and amino acid sequences that identify and encode a human homolog of rat elastase IV (HEIV) expressed in pancreas tissue. The present invention also provides for antisense molecules to the nucleotide sequences which encode HEIV, hybridization probes or oligonucleotides for the detection of HEIV-encoding nucleotide sequences, and a diagnostic test based on HEIV-encoding nucleic acid molecules. The present invention further provides for genetically engineered host cells for the expression of HEIV, biologically active HEIV, antibodies capable for binding specifically to HEIV, and treatment methods comprising administration of compounds, such antibodies or inhibitors, capable of binding HEIV to alter its activity.

5 Claims, 5 Drawing Sheets

```
                11              20              29              38              47              56
5' TTC GGC ACG AGC ATG TTG GGC ATC ACT GTC CTC GCT GCG CTC TTG GCC TGT GCC
   F   G   T   S   M   L   G   I   T   V   L   A   A   L   L   A   C   A 65              74              83              92             101             110
   TCC AGC AGT GGG GTG CCC AGC TTC CCG CCC AAC CTA TCC GCC CGA GTG GTG GGA
   S   S   S   G   V   P   S   F   P   P   N   L   S   A   R   V   V   G 119             128             137             146             155             164
   GGA GAG GAT GCC CGG CCC CAC AGC TGG CCC TGG CAG ATC TCC CTC CAG TAC CTC
   G   E   D   A   R   P   H   S   W   P   W   Q   I   S   L   Q   Y   L 173             182             191             200             209             218
   AAG AAC GAC ACG TGG AGG CAT ACG TGT GGC GGG ACT TTG ATT GAT AGC AAC TTC
   K   N   D   T   W   R   H   T   C   G   G   T   L   I   D   S   N   F 227             236             245             254             263             272
   GTC CTC ACT GCC GCC CAC TGT ATC AGA AAC ACC CGG ACC TAC CGT GTG GCC GTG
   V   L   T   A   A   H   C   I   R   N   T   R   T   Y   R   V   A   V 281             290             299             308             317             326
   GGA AAG AAC AAC CTG GAG GTG GAA GAC GAA GAA GGA TCC CTG TTT GTG GGT GTG
   G   K   N   N   L   E   V   E   D   E   E   G   S   L   F   V   G   V 335             344             353             362             371             380
   GAC ACC ATC CAC GTC CAC AAG AGA TGG AAT GCC CTC CTG TTG CGC AAT GAT ATT
   D   T   I   H   V   H   K   R   W   N   A   L   L   L   R   N   D   I 389             398             407             416             425             434
   GCC CTC ATC AAG CTT GCA GAG CAT GTG GAG CTG AGT GAC ACC ATC CAG GTG GCC
   A   L   I   K   L   A   E   H   V   E   L   S   D   T   I   Q   V   A 443             452             461             470             479             488
   TGC CTG CCA GAG AAG GAC TCC CTG CTC CCC AAG GAC TAC CCC TGC TAT GTC ACC
   C   L   P   E   K   D   S   L   L   P   K   D   Y   P   C   Y   V   T 497             506             515             524             533             542
   GGG TGG GGC CGC CTC TGG ACC AAC GGC CCC ATT GTT GAT AAG CTG CAG CAG GGC
   G   W   G   R   L   W   T   N   G   P   I   V   D   K   L   Q   Q   G 551             560             569             578             587             596
   CTG CAG CCC GTG GTG GAT CAC GCC ACG TGC TCC AGG ATT GAC TGG TGG GGC TTC
   L   Q   P   V   V   D   H   A   T   C   S   R   I   D   W   W   G   F
```

FIG. 1A

```
         605             614             623             632             641             650
AGG GTG AAG AAA ACC ATG GTG TGC GCT GGG GGC GAT GGC GTC ATC TCA GCC TGC
 R   V   K   K   T   M   V   C   A   G   G   D   G   V   I   S   A   C 659             668             677             686             695             704
AAT GGG GAC TCC GGT GGC CCA CTG AAC TGC CAG TTG GAG AAC GGT TCC TGG GAG
 N   G   D   S   G   G   P   L   N   C   Q   L   E   N   G   S   W   E 713             722             731             740             749             758
GTG TTT GGC ATC GTC AGC TTT GGC TCC CGG CGG GGT TGC AAC ACC CGC AAG AAG
 V   F   G   I   V   S   F   G   S   R   R   G   C   N   T   R   K   K 767             776             785             794             803             812
CCG GTA GTC TAC ACC CGG GTG TCC GCC TAC ATC GAC TGG ATC AAC GAG AAA ATG
 P   V   V   Y   T   R   V   S   A   Y   I   D   W   I   N   E   K   M 821             830             839             848             857             866
CAG CTG TGA TTT GTT GCT GGG AGC GGC GGC AGC GAG TCC CTG AAA CAG AAA TAA
 Q   L   *   F   V   A   G   S   G   G   S   E   S   L   K   Q   K   *

875             884
ACT TCC TTC TCC TCG GGG   3'
 T   S   F   S   S   G
```

HOMOLOG OF RAT ELASTASE IV DERIVED FROM HUMAN PANCREAS

This application is a divisional application of U.S. application Ser. No. 08/568,031, filed Dec. 6, 1995.

FIELD OF THE INVENTION

The present invention is in the field of molecular biology; more particularly, the present invention describes the nucleic acid and amino acid sequences of a human homolog of rat elastase IV expressed in the pancreas.

BACKGROUND OF THE INVENTION

Elastases

Elastases are one of several proteolytic enzymes found in the pancreatic juice. Elastase is a member of the serine protease family, a family of proteolytic enzymes that includes other digestive enzymes, such as chymotrypsin and trypsin, and some of the proteases in the blood clotting and complement enzymatic cascades. Members of the serine protease family usually share about 40% homology with other members within the family.

The serine proteases are a class of proteolytic enzymes characterized by the presence of a uniquely reactive serine side chain. The reactive serine group forms a covalent ester bond to the carbonyl carbon atom of a susceptible bond of a polypeptide substrate to form an acyl-enzyme intermediate. Chemical and kinetic studies show that the chemical reactivity of the serine residue is a consequence of a charge relay system, consisting of a histidine side chain imidazole hydrogen bonded to a buried carboxylate of an aspartic acid. The aspartic acid provides the binding site for a proton which, in the transition state, is transferred between nucleophiles, i.e. between the reactive serine of the enzyme and the leaving group of the substrate. This relay system increases the nucleophilicity of the active site serine.

Serine proteases also are characterized by having their catalytically functional groups arranged in the same geometrical relationship. The enzyme binding template is made up of a number of elements acting together: an antiparallel beta-sheet site for binding the substrate polypeptide chain to be acylated, specific side chain binding sites that vary with the particular enzyme; a less specific leaving-group site; a site for hydrogen bonding to a tetrahedral oxyanion; and naturally the reactive serine side chain for covalent binding to a substrate's carbonyl carbon atom.

Polypeptide substrate amino acid residues extending from the cleaved bond toward the N-terminus are typically denoted as P1, P2, P3, and those extending from the cleaved bond toward the C-terminus denoted P'1, P'2, and P'3. The corresponding binding sites on the enzyme are denoted S1, S2, S3, and S'1, S'2, and S'3. Sites S1, S2 and S3 are part of the anti-parallel beta sheet and form part of the crevice for peptide binding. The other wall of the crevice is made up of other backbone peptide links. When a polypeptide substrate is bound at the binding site, the peptide side chains fit into a crevice on the enzyme surface.

Trypsin, the most specific of the serine proteases, attacks preferentially at peptide bonds following an arginine or a lysine at P1. Chymotrypsin rapidly hydrolyzes peptide bonds following an aromatic side chain at P1. Elastase does not display quite a marked specificity, but generally prefers an uncharged nonaromatic side chain especially alanine at the P1 position. In elastase, the crevice is partially occluded by the side chain of Val-216, and the bottom of the crevice is partly filled by the side chain of threonine-226, leaving room for binding of small P1 side chains only. Because of the small binding energy available from the interaction between the P1 side chain and the crevice surface in elastase, catalysis is more dependent upon enzyme substrate contacts remote from the cleaved bond.

Proteolytic Enzyme Secretion from the Pancreas

The pancreas consists in part of exocrine tissue. Acinar cells are derived from exocrine tissue and function in the secretion of numerous pancreatic enzymes which assist digestion in the gastrointestinal tract. The proteolytic enzymes secreted by the acinar cells include elastase, trypsin, chymotrypsin, and carboxypeptidase. Trypsin, chymotrypsin, and elastase split whole and partially-digested proteins into polypeptides of different sizes; then, carboxypeptidase breaks down the polypeptides into individual amino acids. The principal enzyme for digesting carbohydrates in the gut is pancreatic amylase. It hydrolyses starches, glycogen, and most other non-cellulosic carbohydrates to form disaccharides and trisaccharides. The main enzymes for fat digestion are pancreatic lipase, cholesterol esterase, and phospholipase. Pancreatic lipase hydrolyses neutral fat into fatty acids and monoglycerides. Cholesterol esterase hydrolyses cholesterol esters, and phospholipase removes fatty acid molecules from phospholipids.

Pancreatic cells secrete the proteolytic enzymes as inactive forms, such as trypsinogen, chymotrypsinogen, procarboxypeptidase, and proelastase. These enzymes are not activated until they reach the duodenum. Secretion of enterokinase from the intestinal mucosa is triggered by chyme entering the duodenum. Trypsinogen is activated by enterokinase or existing duodenal trypsin. Both chymotrypsinogen, procarboxypeptidase and proelastase are primarily activated by trypsin. Along with the inactive proteolytic enzymes, the acinar cells also secrete trypsin inhibitor. Trypsin inhibitor prevents the activation of the proteolytic enzymes inside acinar cells and pancreatic ducts.

Four molecules control proteolytic enzyme secretion from the pancreas: acetylcholine and the hormones, gastrin, cholecystokinin (CCK), and secretin. Acetylcholine, gastrin, and CCK all stimulate the acinar cells of the pancreas to secrete enzymes. These three molecules also stimulate the ductal cells to secrete sodium bicarbonate and water. Secretin, however, stimulates the secretion of large quantities of this sodium bicarbohate "solution" which serves to wash/move pancreatic enzymes through the various ducts into the duodenum.

Acetylcholine is released from the parasympathetic vagus nerve endings and other cholinergic nerves of the enteric nervous system. CCK and secretin are secreted by the duodenal and upper jejunal mucosa when chyme enters the small intestine. CCK occurs in several forms. The most common are the 8- and 33-amino acid forms. CCK molecules are released from cells of the duodenal and jejunal mucosa. Proteases and peptones from partial digestion of proteins and long chain fatty acids stimulate the release and transport of CCK. In the pancreas, CCK interacts with specific acinar cell-surface receptors. Via the phosphoinositol pathway, the CCK- receptor complex mobilizes intracellular $Ca^{2+}$ and cyclic guanosine monophosphate (cGMP) which in turn activates protein kinase. Secretin has 27 amino acids and interacts with specific cell membrane receptors of the ductal cells. The receptors activate an intracellular cyclic adenine monophosphate (cAMP) system which stimulates cellular secretion.

Pancreatic secretion occurs in three different phases, the cephalic, gastric, and intestinal phases. During the cephalic phase, a nerve stimulates secretion in the stomach and release of acetylcholine from vagal nerve endings in the pancreas. Acetylcholine governs the release of moderate amounts of enzymes. Because very little water and sodium bicarbonate are secreted during this phase, only small amounts of enzyme are washed into the duodenum.

During the gastric phase, large amounts of gastrin formed in the stomach stimulate the pancreas to secrete more enzymes. Still, lack of water and sodium bicarbonate assure that very small quantities of enzymes reach the duodenum. It is during the intestinal phase, when chyme enters the duodenum, that secretin is produced and transported to the pancreas. There secretin stimulates the release of large quantities of sodium bicarbonate solution which wash the enzymes into the duodenum. At this time, the mechanisms for the active transport of sodium ions ($Na^+$) and bicarbonate ions are not fully understood, but it has been suggested that active transport of sodium ions is accomplished by a $Na^+$, $H^+$-ATPase at the apical membrane. CCK also stimulates increased pancreatic enzyme secretion during this last phase.

Inhibition during the cephalic phase involves the counteraction of parasympathetic innervation by sympathetic innervation. However, norepinephrine has no effect on basal pancreatic secretion. During the gastric phase, any factor which directly affects the retention of chyme in the stomach will prevent or reduce the secretion of CCK and secretin. If fat is introduced into the ileum during the intestinal phase, an unidentified hormonal factor has been shown to inhibit pancreatic secretion.

Excessive active serine protease production, including elastase production, may result in tissue wasting. For example, acute pancreatitis may result by the activation of proteolytic enzymes within the pancreas. A number of factors, such as endotoxins, exotoxins, viral infections, ischemia, anoxia and direct trauma, are believed to activate these proenzymes. The active enzymes then digest cellular membranes and cause edema, interstitial hemorrhage, vascular damage, coagulation necrosis, fat necrosis, and parenchymal cell necrosis. On the other hand, very low levels of serine protease production may indicate the destruction of acinar cells.

SUMMARY OF THE INVENTION

The present invention relates to a novel human homolog of rat elastase IV (HEIV) isolated from human pancreas and to the use of this novel protein and its nucleic acid sequence in the diagnosis, prevention and treatment of disease states or conditions associated with excessive tissue wasting. The nucleotide sequences disclosed herein can also be used for in vitro purposes related to synthesis of DNA, manufacture of DNA vectors and the production of protein. The complete polynucleotide sequence encoding HEIV is disclosed herein, and provides the basis for several aspects of the invention hereinafter described.

The present invention provides cloning or expression vectors comprising a polynucleotide sequence encoding HEIV, and host cells or organisms transformed with expression vectors comprising the polynucleotide sequence.

The polynucleotide sequences disclosed herein may be used in diagnostic assays to detect and quantify levels of HEIV mRNA in cells and tissues. For example, an HEIV encoding polynucleotide sequence may be used in hybridization assays of biopsied tissue to diagnose abnormalities in gene expression associated with diseases or conditions associated with excessive tissue wasting.

A further aspect of the present invention relates to HEIV antisense molecules which can be used to inhibit translation of heiv mRNA.

The present invention provides a method for the production and recovery of purified HEIV from host cells. Purified HEIV can be used for the production of anti-HEIV antibodies. Anti-HEIV antibodies may be used for diagnostic purposes for the detection of HEIV in tissues and cells or in screening assays for the detection of inhibitors of HEIV activity. Anti-HEIV antibodies may also be used for therapeutic purposes, for example, in neutralizing the activity of HEIV associated with diseases or conditions associated with excessive tissue wasting. The present invention also relates in part to proteins, peptides and organic molecules capable of modulating activity of HEIV which may be used therapeutically in the treatment of disease states associated with excessive tissue wasting.

The present invention also relates to pharmaceutical compositions for the treatment of disease states associated with aberrant expression of HEIV comprising HEIV antisense molecules, anti-HEIV or other proteins, peptides, or organic molecules capable of modulating HEIV expression.

DESCRIPTION OF THE FIGURES

FIGS. 1A and 1B display the nucleotide sequence and predicted amino acid sequence for the coding region of the human homolog of elastase IV (HEIV) included in Incyte Clone 226990.

FIGS. 2A and 2B shows the amino acid alignment of HEIV with rat elastase IV. Alignments shown were produced using the multisequence alignment program of DNASTAR software (DNASTAR Inc, Madison Wis.).

DETAILED DESCRIPTION OF THE INVENTION

Definitions

Figure 3:
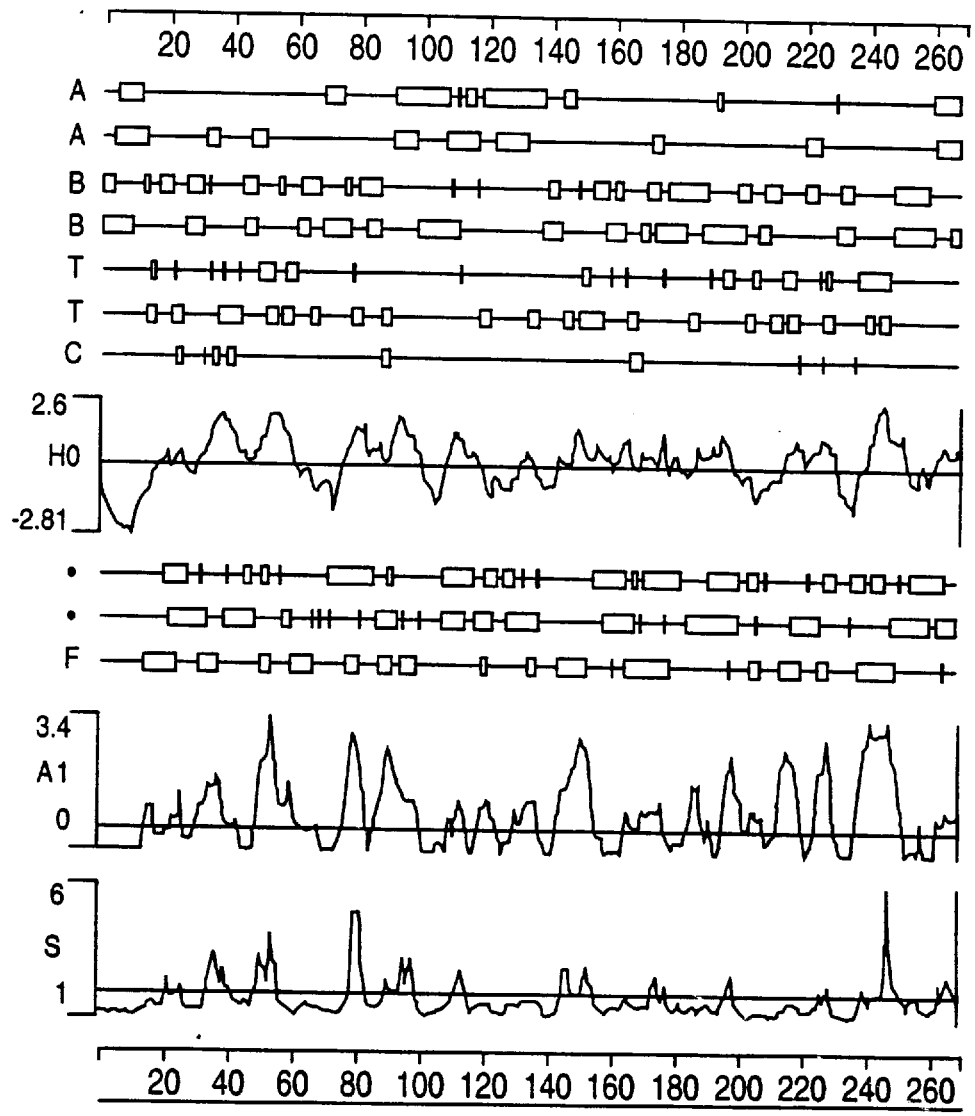
FIG. 3 provides structural analysis of the HEIV amino acid sequence for determining putative alpha (A), beta (B), turn (T), and coil (C) regions; a hydrophilicity plot (H); alpha and beta amphipathic regions (*); flexible regions (F); a putative antigenic index (AI); and a surface probability plot (S) using the structural analysis program of DNASTAR software (DNASTAR Inc, Madison Wis.).

The present invention provides a unique nucleotide sequence which encodes a human homolog of rat elastase IV isolated from human pancreas. The human homolog is called HEIV. As used herein, the lower case letters, heIV, refer to a gene, cDNA or nucleic acid sequence while the upper case letters, HEIV, refer to a protein, polypeptide, peptide, oligopeptide, or amino acid sequence.

An "oligonucleotide" is a portion of a DNA sequence which has a sufficient number of bases to be used as an oligomer, amplimer or primer in a polymerase chain reaction (PCR). Oligonucleotides are prepared from genomic or cDNA sequences and are used to amplify, confirm, or reveal the presence of an identical or similar DNA or RNA in a particular cell or tissue. Oligonucleotides comprise portions of a DNA sequence having at least about 10 nucleotides and as many as about 50 nucleotides, preferably about 15 to 30 nucleotides.

A "fragment" of a polynucleotide or nucleic acid comprises all or any part of the nucleotide sequence having fewer nucleotides than about 6 kb, preferably fewer than about 1 kb, which can be used as a probe, can be therapeutically active, or can be used to synthesize a polypeptide fragment. Probes are useful in the detection of identical, similar, or complementary nucleic acid sequences. Longer length probes are highly specific, but slow to hybridize. Shorter length probes are quick to hybridize, but must be carefully designed to have specificity. Single- or double-stranded probes may be either chemically synthesized or obtained and/or modified from naturally occurring or recombinant sequences. Such probes may be labelled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Reporter" or "label" molecules are chemical moieties used for labelling a nucleic or an amino acid sequence. They include, but are not limited to, radionuclides, enzymes, fluorescent, chemiluminescent, or chromogenic agents. Reporter molecules associate with particular nucleic acid or amino acid sequence for determining its presence or its quantity in a sample.

A "recombinant nucleotide variant" is a nucleotide sequence that has been altered from that which occurs naturally, various codon substitutions, such as the silent changes which produce specific restriction sites or codon usage-specific mutations, may be introduced to optimize cloning into a plasmid or viral vector or expression in a particular prokaryotic or eukaryotic host system, respectively. In particular the sequence encodes a polypeptide which may be synthesized by making use of the "redundancy" in the genetic code. Recombinant nucleotide variants also include nucleotide sequences with the necessary nucleic acid substitutions, insertions and/or deletions to produce recombinant polypeptide variants (described below).

"Linkers" are palindromic oligomers which create internal restriction endonuclease sites for ease of cloning the genetic material of choice into various vectors.

The term "chimeric molecule", as used herein, refers to polynucleotides or polypeptides which are created by combining one or more nucleotide sequences of this invention with additional nucleic acid sequence(s). Such combined sequences may be introduced into an appropriate vector for expression of a chimeric polypeptide. Examples of useful chimeric polypeptides are those with changes in cellular location, distribution, ligand-binding affinities, interchain affinities, degradation/turnover rate, signalling, etc.

"Active" describes a molecular state of a molecule which is capable of initiating some process or of carrying out some role. In this application it specifically refers to those forms, fragments, or domains of an amino acid sequence which display biologic and/or immunogenic properties characteristic of the naturally occurring polypeptide.

"Naturally occurring HEIV" refers to a polypeptide produced by cells which have not been genetically engineered or which have been genetically engineered to produce the same sequence as that naturally produced. Specifically contemplated are various polypeptides which are post-translationally modified. Such modifications of the polypeptide include but are not limited to acetylation, carboxylation, glycosylation, phosphorylation, lipidation and acylation.

"Derivative" refers to a polypeptide which has been chemically modified by such techniques as ubiquitination, labelling (see above), pegylation (derivatization with polyethylene glycol), and chemical insertion, deletion, or substitution of amino acids. It comprises substitutions of amino acids such as ornithine which do not normally occur in human proteins.

"Recombinant polypeptide variant" refers to any polypeptide which differs from naturally occurring HEIV by amino acid insertions, deletions and/or substitutions, created using recombinant DNA techniques. Guidance in determining which amino acid residues may be replaced, added or deleted without abolishing characteristics of interest may be found by comparing the sequence of HEIV with that of related polypeptides and minimizing the number of amino acid changes in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are additions or eliminations of amino acids from polypeptides. Such changes typically involve about 1 to 5 amino acids. The variation allowed in a particular amino acid sequence may be experimentally determined by producing the peptide synthetically or by systematically making insertions, deletions, or substitutions of nucleotides in the heIV sequence using recombinant DNA techniques.

A "signal or leader sequence" is a short amino acid sequence which directs, or can be used to direct, the polypeptide through the membrane of a cell. Such a sequence may be naturally present on the polypeptides of the present invention or provided from heterologous sources and added to the polypeptide by recombinant DNA techniques.

An "oligopeptide" is a short stretch of amino acid residues and may be expressed from an oligonucleotide. It may be considerably shorter than or the same length as a "fragment," "portion," or "segment" of a polypeptide. An oligopeptide comprises a stretch of amino acid residues of at least about 5 amino acids and often about 17 or more amino acids, typically at least about 9 to 13 amino acids, and of sufficient length to display biologic and/or immunogenic activity.

A "standard" is a quantitative or qualitative measurement of a compound at a known concentration used for comparing samples with unknown concentrations of the same or related compounds. Preferably, it is based on a statistically appropriate number of samples and is created to use as a basis of comparison when performing diagnostic assays. Diagnostic assays may in turn be used for monitoring clinical trials, or following patient treatment profiles.

"Animal" as used herein may be defined to include human, domestic (cats, dogs, etc.), agricultural (cows, fish, horses, sheep, chickens, etc) or test species (amphibian, rodent, simian, etc).

Since the list of technical and scientific terms cannot be all encompassing, any undefined terms shall be construed to have the same meaning as is commonly understood by one of ordinary skill in the art to which this invention belongs. Furthermore, the singular forms "a", "an" and "the" include plural referents unless the context clearly dictates otherwise. For example, reference to a "high-fidelity enzyme" includes mixtures of such enzymes and any other enzymes fitting the stated criteria, and reference to "the method" includes reference to one or more methods for doing the same thing, which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

Detailed Description of the Invention

The present invention provides a unique polynucleotide sequence which encodes a homolog of the rat elastase IV derived from human pancreas tissue. The human homolog sequence is called heIV. The polynucleotide sequence was first identified in Incyte Clone 226990. Incyte Clone 226900 contained only a partial sequence for heIV. To obtain the full length heIV sequence, the sequence was assembled from the inserts of additional Incyte Clones derived from normal and diabetic human pancreas libraries. The clone sequences were assembled to create a sequence which comprises the whole heIV full-length sequence including 5'-and 3'-sequences, based on Incyte Clone 226900. Table 1 in the Examples lists the clones that were used to assemble the whole full length sequence, including their clone number and source. As a final step the full-length heIV polynucleotide was resequenced for assurance of an accurate full-length sequence. The sequence of 226900 is shown in SEQ ID NO. 1. The coding sequence is shown from nucleotide 22 to 828 of SEQ ID NO.1 and from nucleotide 15 to 821 of FIG. 1.

The purified nucleic acid sequence for heIV has numerous applications in techniques known to those skilled in the art of molecular biology. These applications include its use as a hybridization probe, for chromosome and gene mapping, in PCR technologies, in the production of sense or antisense nucleic acids, in screening for new therapeutic molecules, etc. These examples are well known and are not intended to be limiting. Furthermore, heIV may be used in molecular biology techniques that have not yet been developed, provided the new techniques rely on properties of nucleotide sequences that are currently known such as the triplet genetic code, specific base pair interactions, etc.

As a result of the degeneracy of the genetic code, a multitude of HEIV-encoding nucleotide sequences may be produced and some of these will bear only minimal homology to the endogenous sequence of any known and naturally occurring heIV. This invention has specifically contemplated each and every possible variation of nucleotide sequence that could be made by selecting combinations based on possible codon choices.

Although the heIV nucleotide sequence and its derivatives or variants are preferably capable of identifying the nucleotide sequence of the naturally occurring heIV under optimized conditions, it may be advantageous to produce heIV nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the heIV nucleotide sequence without altering the encoded amino acid sequence include the production of RNA transcripts having more desirable properties, such as a longer half-life, than transcripts produced from the naturally occurring sequence.

Nucleotide sequences for heIV may be joined to a variety of other nucleotide sequences by means of well established recombinant DNA techniques (Sambrook J et al (1989) *Molecular Cloning: A Laboratory Manual*, Cold Spring Harbor Laboratory, Cold Spring Harbor, N.Y.; or Ausubel F M et al (1989) *Current Protocols in Molecular Biology*, John Wiley & Sons, New York City). Useful sequences for joining to heIV include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

PCR as described in U.S. Pat. Nos. 4,683,195; 4,800,195; and 4,965,188 provides additional uses for oligonucleotides based upon the heIV nucleotide sequence. Such oligomers are generally chemically synthesized, but they may be of recombinant origin or a mixture of both. Oligomers may comprise two nucleotide sequences employed under optimized conditions for tissue specific identification or diagnostic use. The same two oligomers, nested sets of oligomers, or even a degenerate pool of oligomers may be employed under less stringent conditions for identification and/or quantitation of closely related DNA or RNA sequences.

Full length genes may be cloned utilizing partial nucleotide sequence and various methods known in the art. "Restriction-site PCR" is a direct method (Gobinda et al (1993) *PCR Methods Applic.* 2:318–22) which uses universal primers to retrieve unknown sequence adjacent to a known locus. First, genomic DNA is amplified in the presence of high fidelity enzymes, a primer adjacent to linker, and a primer specific adjacent to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR (Triglia T et al (1988) *Nucleic Acids Res.* 16:8186) is the first method to report successful acquisition of unknown sequences starting with primers based on a known region. The method uses several restriction enzymes to generate a suitable fragment in the known region of a gene. The fragment is then circularized by intramolecular ligation and used as a PCR template. Divergent primers are designed to prime outward from the known region and multiple rounds of restriction enzyme digestions and ligations are necessary.

Capture PCR (Lagerstrom M et al (1991) *PCR Methods Applic.* 1:111–19) is a method for PCR amplification of DNA fragments adjacent to a known human sequence in a yeast artificial chromosome (YAC). Capture PCR also requires multiple restriction enzyme digestions and ligations to place an engineered double-stranded sequence into an unknown portion of the DNA molecule before PCR. This method allows the restriction and ligation reactions to be carried out simultaneously and further requires extension, immobilization, two rounds of PCR and purification prior to sequencing.

Walking PCR (Parker J D et al (1991) *Nucleic Acids Res.* 19:3055–60) is a method for targeted gene walking for the retrieval of unknown sequence. It requires oligomer-extension assay followed by gel purification and identification of the desired fragment prior to sequencing. Promoter-Finder™ is a new kit available from Clontech (Palo Alto, Calif.) which uses PCR and primers derived from p53 to walk in genomic DNA. Nested primers and special PromoterFinder libraries are used to detect upstream sequences such as promoters and regulatory elements. This process avoids the need to screen libraries and is useful in finding intron/exon junctions.

A new method which employs XL-PCR (Perkin-Elmer, Foster City, Calif.) amplifies and extends partial nucleotide sequence into long pieces of DNA. This method was developed to allow a single researcher to process multiple genes (up to 20 or more) at a time and to obtain an extended (possibly full-length) sequence within 6–10 days. This new method replaces methods which use labelled probes to screen plasmid libraries and allow one researcher to process only about 3–5 genes in 14–40 days. A description of the method is provided in co-pending application Ser. No. 08/487,112 filed Jun. 7, 1995, entitled "Improved Method for Obtaining Full Length cDNA Sequences", which is herein incorporated by reference.

In the first step, which can be performed in about two days, any two of a plurality of primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones.

If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg, Md.). The cDNA library may have been prepared with oligo (dT) or random priming. Random primed libraries are preferred in that they will contain more sequences which contain 5' ends of genes. A randomly primed library may be particularly useful if an oligo (dT) library does not yield a complete gene. It must be noted that the larger and more complex the protein, the less likely it is that the complete gene will be found in a single plasmid.

A new method for analyzing either the size or the nucleotide sequence of PCR products is capillary electrophoresis. Systems for rapid sequencing are available from Perkin Elmer (Foster City Calif.), Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis provides greater resolution and is many times faster than standard gel based procedures. It is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) *Anal Chem* 65:2851–8).

Another aspect of the subject invention is to provide for an heIV hybridization probe which is capable of hybridizing with naturally occurring nucleotide sequences for heIV. The stringency of the hybridization conditions will determine whether the probe identifies only the native heIV sequence or a sequence of closely related molecules. If a degenerate heIV sequence of the subject invention is used for the detection of related sequences, it should preferably contain at least 50% of the nucleotides of the sequence presented herein. Hybridization probes may be derived from the nucleotide sequence of the SEQ ID NO:1, or from surrounding or included genomic sequences comprising untranslated regions such as promoters, enhancers and introns. Such hybridization probes may be labelled with appropriate reporter molecules.

Means for producing specific hybridization probes for heIV include oligolabelling, nick translation, end-labelling or PCR amplification using a labelled nucleotide. Alternatively, the cDNA sequence may be cloned into a vector for the production of mRNA probe. Such vectors are known in the art, are commercially available, and may be used to synthesize RNA probes in vitro by addition of an appropriate RNA polymerase such as T7, T3 or SP6 and labelled nucleotides. A number of companies which develop molecular biology products (such as Pharmacia Biotech, Piscataway, N.J.; Promega, Madison, Wis.; USB, Cleveland, Ohio, etc.) supply commercial kits and protocols for these various procedures.

It is also possible to produce a DNA sequence, or portions thereof, entirely by synthetic chemistry. Sometimes the source of information for producing this sequence comes from a known homologous sequence from a closely related organism. After synthesis, the nucleic acid sequence can be used alone or joined with other sequence(s) and inserted into one of the many available DNA vectors and their respective host cells using techniques well known in the art. Moreover, synthetic chemistry may be used to introduce specific mutations into the nucleotide sequence. Alternatively, a portion of sequence in which a mutation is desired can be synthesized and recombined with a portion of an existing genomic or recombinant sequence.

The nucleotide sequence for heIV can be used in an assay to detect conditions associated with altered heIV genomic sequences or altered levels of heIV mRNA in pancreas or other tissues. The cDNA can be labeled by methods known in the art and added to a fluid, cell or tissue sample from a patient under hybridizing conditions. After an incubation period, the sample is washed with a compatible fluid which optionally contains a reporter molecule. After the compatible fluid is rinsed off, the reporter molecule is quantitated and compared with a standard as previously defined. If heIV mRNA levels are significantly different from normal levels, the assay may indicate an abnormal response to environmental stress or abnormal cellular proliferation.

This same assay, combining a sample with the nucleotide sequence, is applicable in evaluating the efficacy of a particular therapeutic treatment. It may be used in animal studies, in clinical trials, or in monitoring the treatment of an individual patient. First, standard expression must be established for use as a basis of comparison. Second, samples from the animals or patients affected by the disease are combined with the nucleotide sequence to evaluate the deviation from the standard or normal profile. Third, an existing therapeutic agent is administered, and a treatment profile is generated. The assay is evaluated to determine whether the profile progresses toward or returns to the standard pattern. Successive treatment profiles may be used to show the efficacy of treatment over a period of several days or several months.

The heIV nucleotide sequence can also be used to generate probes for mapping the native gene. The sequence may be mapped to a particular chromosome or to a specific region of the chromosome using well known techniques. These include in situ hybridization to chromosomal spreads (Verma et al (1988) *Human Chromosomes: A Manual of Basic Techniques*, Pergamon Press, New York City), flow-sorted chromosomal preparations, or artificial chromosome constructions such as YACs, bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in the 1994 Genome Issue of *Science* (265:1981f). Often the placement of a gene on the chromosome of another mammalian species may reveal associated markers even if the number or arm of a particular human chromosome is not known. New partial nucleotide sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) *Nature* 336:577–580), any sequences mapping to that area may represent genes for further investigation. The nucleotide sequences of the subject invention may also be used to detect differences in the chromosomal location of nucleotide sequences due to translocation, inversion, etc. between normal and carrier or affected individuals.

The heIV nucleotide sequence may be used to produce an amino acid sequence using well known methods of recombinant DNA technology (Goeddel (1990) Gene Expression Technology, *Methods in Enzymology*, Vol 185, Academic Press, San Diego, Calif.). The HEIV amino acid sequence or a fragment thereof may be expressed in a variety of host cells, either prokaryotic or eukaryotic. Host cells may be from the same species from which the nucleotide sequence was derived or from a different species. Advantages of producing an amino acid sequence or peptide by recombinant DNA technology include the availability of simplified purification procedures to generate large quantities of polypeptide or fragments thereof.

Cells transformed with heIV may be cultured under conditions suitable for the expression and recovery of the polypeptide from cell culture. The polypeptide produced by a recombinant cell may be secreted or may be contained intracellularly depending on the sequence itself and/or the vector used. In general, it is more convenient to prepare recombinant polypeptides in secreted form, and this is accomplished by ligating heIV to a recombinant nucleotide sequence which directs its movement through a particular prokaryotic or eukaryotic cell membrane. Other chimeric constructions may join heIV to nucleotide sequence encoding a polypeptide domain which will facilitate protein purification (Kroll D J et al (1993) DNA Cell Biol 12:441–53).

Direct peptide synthesis using solid-phase techniques (Stewart et al (1969) *Solid-Phase Peptide Synthesis,* WH Freeman Co, San Francisco, Calif.; Merrifield J (1963) *J Am Chem Soc* 85:2149–2154) is an alternative to recombinant or chimeric peptide production. Automated synthesis may be achieved, for example, using Applied Biosystems 431A Peptide Synthesizer (Foster City, Calif.) in accordance with the instructions provided by the manufacturer. Additionally the HEIV sequence or any fragment thereof may be mutated during direct synthesis and, if desired, combined using chemical methods with other amino acid sequences.

Another aspect of the subject invention is the use of HEIV specific antibodies to control excessive production of proelastase or elastase, particularly elastase. These antibodies therefore are particularly useful to control tissue wasting during acute pancreatitis when elastase is activated in the pancreas instead of in the gastrointestinal tract. HEIV used to induce specific antibodies may have an amino acid sequence consisting of at least five amino acids and preferably at least 10 amino acids. Short stretches of amino acid sequence may be attached with those of another protein, and the chimeric peptide used for antibody production. Alternatively, the oligopeptide may be of sufficient length to contain an entire domain for antibody recognition.

Antibodies specific for HEIV may be produced by inoculation of an appropriate animal with an antigenic fragment of the peptide. An antibody is specific for HEIV if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (Orlandi R et al (1989) *Proc. Natl. Acad. Sci. USA* 86:3833–3837, or Huse W D et al (1989) *Science* 256:1275–1281), or the in vitro stimulation of lymphocyte populations.

Current technology (Winter G and Milstein C (1991) *Nature* 349:293–299) provides for a number of highly specific binding reagents based on the principles of antibody formation. These techniques may be adapted to produce molecules which specifically bind HEIV. Antibodies or other appropriate molecules generated against a specific immunogenic peptide fragment or oligopeptide can be used in Western analysis, enzyme-linked immunosorbent assays (ELISA) or similar tests to establish the presence of or to quantitate amounts of HEIV active in normal, diseased, or therapeutically treated cells or tissues. Variations on any procedure known in the art for the measurement of HEIV can be used in the practice of the instant invention. Such procedures include but are not limited to competitive and non-competitive assay systems using techniques such as radioimmunoassays, ELISA (enzyme linked immunoabsorbent assay), sandwich immunoassays, agglutination assays, complement fixation assays, immunoradiometric assays, fluorescent immunoassays, protein A immunoassays, and immunoelectrophoresis assays.

Various procedures known in the art may be used for the production of antibody, various host cells may be immunized with the antigen, a synthetic fragment, or a recombinant version thereof. Various adjuvants may be used to increase the immunological response, depending on the host species, and including but are not limited to Freund's adjuvant (complete and incomplete), mineral gels such as aluminum hydroxide, surface active substances such as lysolecithin, polyanions, peptides, oil emulsion, keyhole limpet hemocyanin, dinitrophenol, or liposomes.

A monoclonal antibody can be prepared by using any technique which provides for the production of antibody molecules by continuous cell lines in cultures. These include but are not limited to the hybridoma technique originally described by Kohler and Milstein (1975) *Nature* 256:495–497), the more recent human B cell hybridoma technique (Kozbor et al (1983) *Immunol Today* 4;72) and EBV-hybridoma technique (Cole et al (1985) *Monoclonal Antibodies and Cancer Therapy,* Alan R. Liss, Inc).

In one embodiment, the monoclonal antibodies may be human monoclonal antibodies, chimeric human-mouse (or other species), or humanized antibodies. Human monoclonals may be made by any of numerous techniques known in the art (Kozbor). Chimeric antibody molecules may be prepared containing a mouse (or other species) antigen-binding domain with human constant regions (Morrison et al. (1984) *Proc. Natl. Acad. Sci. USA* 81:6852). Humanized antibodies may be recombinantly prepared such that only the hypervariable domains are non-human sequences.

Kits for carrying out the assays are also within the scope of the invention. A kit for detecting HEIV can be prepared for routine use. Such a kit would include wells to receive a sample from an individual. Each well contains a reagent capable of binding HEIV selectively, particularly a monoclonal antibody against purified HEIV or a fragment thereof. In addition the kits may contain a detection antibody, washing solutions, and a substrate used for generating a colored solution from the detection solution. The kits naturally include both negative and positive controls. The negative control is a sample lacking HEIV. The positive controls are samples with known concentrations of HEIV from which a standard curve can be derived.

Administration of antibodies against or inhibitors of HEIV may control tissue wasting. Therapeutic compositions comprising either antibodies or inhibitors may be administered in a suitable therapeutic dose determined by any of several methodologies including clinical studies on mammalian species to determine maximal tolerable dose and on normal human subjects to determine safe dose. Additionally, the therapeutic compound may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating stress-related disorders.

The examples below are provided to illustrate the subject invention. These examples are provided by way of illustration and are not included for the purpose of limiting the invention.

EXAMPLES

I cDNA Library Construction

A normal pancreas tissue sample (obtained from IIAM, Exton, Pa., lot RV94-0806) from a 29 year old Caucasian male, expiring from head trauma, was used. The tissue was flash frozen in liquid nitrogen, ground in a mortar and pestle, and lysed immediately in a buffer containing guanidinium isothiocyanate. Lysates were then loaded on a 5.7M CsCl cushion and ultracentrifuged in a SW28 swinging bucket rotor for 18 hours at 25000 rpm at ambient temperature. Total RNA was then ethanol precipitated, washed in 70% ethanol and resuspended in distilled water and DNAse for 15 minutes at 37° C. The RNA was acid phenol extracted and ethanol precipitated. After being washed in 70% ethanol, the polyadenylated RNA was isolated using Oligotex™ resin with spherical latex particles (QIAGEN Inc., Chatsworth, Calif.) and quantitated and frozen at −80° C. The isolated RNA was sent to Stratagene, La Jolla, Calif. for cDNA library preparation.

Synthetic adaptor oligonucleotides were ligated onto cDNA ends enabling its insertion into Uni-ZAP™ vector system (Stratagene), allowing high efficiency unidirectional (sense orientation) lambda library construction and the convenience of a plasmid system with blue/white color selection to detect clones with cDNA insertions. Finally, the two libraries were combined into a single library by mixing equal numbers of bacteriophage.

The pancreas cDNA library can be screened with either DNA probes or antibody probes and the pBluescript phagemid (Stratagene) can be rapidly excised in vivo. The phagemid allows the use of a plasmid system for easy insert characterization, sequencing, site-directed mutagenesis, the creation of unidirectional deletions and expression of fusion polypeptides. The custom-constructed library phage particles were infected into *E. Coli* host strain XL1-Blue® (Stratagene), which has a high transformation efficiency, increasing the probability of obtaining rare, under-represented clones in the cDNA library. Alternative unidirectional vectors include but are not limited to pcDNAI (Invitrogen, San Diego, Calif.) and pSHlox-1 (Novagen, Madison, Wis.).

A pancreas tissue sample from a 15 year old Caucasian male with insulin dependent juvenile diabetic mellitus (Type I) was also obtained from IIAM (Lot GJD-886). He had been receiving insulin treatment before his death. The patient expired from a single gun shot wound to the head. A library for this sample was prepared as described above.

II Isolation of cDNA Clones

The phagemid forms of individual cDNA clones were obtained by the in vivo excision process, in which the host bacterial strain was coinfected with both the λlibrary phage and an f1 helper phage. Polypeptides or enzymes derived from both the library-containing phage and the helper phage nicked the λDNA, initiated new DNA synthesis from defined sequences on the λtarget DNA and created a smaller, single stranded circular phagemid DNA molecule that included all DNA sequences of the pBLUESCRIPT® plasmid and the cDNA insert. The phagemid DNA was secreted from the cells and purified, then used to re-infect fresh host cells, where the double stranded phagemid DNA was produced. Because the phagemid carries the gene for β-lactamase the newly transformed bacteria were selected on medium containing ampicillin.

Phagemid DNA was purified using the MAGIC MINI-PREPS™ DNA Purification System (Promega catalogue #A7100, Promega Corporation, Madison, Wis.). This small-scale process provides a simple and reliable method for lysing the bacterial cells and rapidly isolating purified phagemid DNA using a proprietary DNA-binding resin. The DNA was eluted from the purification resin already prepared for DNA sequencing and other analytical manipulations.

Phagemid DNA was also purified using the QIAWELL-8 Plasmid Purification System from QIAGEN®, QIAWELL PLUS and QIAWELL ULTRA DNA Purification System (QIAGEN Inc., Chatsworth, Calif. ). This product line provides a convenient, rapid and reliable high-throughput method for lysing the bacterial cells and isolating highly purified phagemid DNA using QIAGEN anion-exchange resin particles with EMPORE™ membrane technology from 3M in a multiwell format.

III Sequencing of CDNA Clones

The cDNA inserts from random isolates of the normal pancreas and insulin dependent diabetes mellitus pancreas were sequenced. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 377 or 373 DNA sequencer). Alternatively, cDNA inserts may be sequenced using a Hamilton Micro Lab 2200 (Hamilton, Reno, Nev.) in combination with four Peltier Thermal Cyclers (PTC200 from MJ Research, Watertown, Mass.) along with Applied Biosystems 377 or 373 DNA Sequencing System.

IV Assemblage of Clones Inserts to Obtain the Full Length Sequence

Incyte Clone 226990 was the first clone identified to contain the partial sequence of a human homolog of the rat elastase IV gene including the coding start site ATG. This insert was used to screen the normal pancreas library and the insulin dependent diabetes mellitus pancreas library for contiguous sequences. Once clones were identified containing more 3' sequence, those sequences were used to screen the two libraries again to identify other contiguous sequences. Eventually, thirty-three additional clones which contained contiguous sequences were identified to assemble the full-length sequence for the coding sequence for HEIV. Table 1 lists all the clones and the library they originated from: either the normal pancreas library (PANCNOT01) or the insulin dependent diabetes mellitus pancreas library (PANCDIT01 or IDDM). The table also describes the length of the assembled sequence (nucleotides 22 to 828) and the start site and length of each individual clone.

sons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments of the protein sequence were used to display the results of the homology search.

Peptide and protein sequence homologies were ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, was used to search for local sequence alignments (Altschul S F (1993) *J Mol Evol* 36:290–300; Altschul, S F et al (1990) *J Mol Biol* 215:403–10). BLAST produces alignments of both nucle-

TABLE 1

| clone | locus | library | description | RI Start | RI End | start | length |
|---|---|---|---|---|---|---|---|
| 226990 | RNELASIV | PANCNOT01 | Elaslase | 22 | 828 | 22 | 199 |
| 222049 | RNELASIV | PANCNOT01 | Elaslase | 22 | 828 | 25 | 145 |
| 223063 | RNELASIV | PANCNOT01 | Elaslase | 22 | 828 | 28 | 330 |
| 222016 | RNELASIV | PANCNOT01 | Elaslase | 22 | 828 | 38 | 189 |
| 228058 | RNELASIV | PANCNOT01 | Elaslase | 22 | 828 | 102 | 188 |
| 227132 | RNELASIV | PANCNOT01 | Elaslase | 22 | 828 | 104 | 233 |
| 229523 | RNELASIV | PANCNOT01 | Elaslase | 22 | 828 | 105 | 427 |
| 228572 | RNELASIV | PANCNOT01 | Elaslase | 22 | 828 | 152 | 189 |
| 227781 | RNELASIV | PANCNOT01 | Elaslase | 22 | 828 | 161 | 199 |
| 251008 | RNELASIV | PANCDIT01 | Elaslase | 22 | 828 | 173 | 223 |
| 226307 | RNELASIV | PANCNOT01 | Elaslase | 22 | 828 | 221 | 243 |
| 227194 | RNELASIV | PANCNOT01 | Elaslase | 22 | 828 | 222 | 193 |
| 223240 | RNELASIV | PANCNOT01 | Elaslase | 22 | 828 | 224 | 213 |
| 227261 | RNELASIV | PANCNOT01 | Elaslase | 22 | 828 | 259 | 242 |
| 222726 | RNELASIV | PANCNOT01 | Elaslase | 22 | 828 | 327 | 217 |
| 222765 | RNELASIV | PANCNOT01 | Elaslase | 22 | 828 | 327 | 172 |
| 226359 | RNELASIV | PANCNOT01 | Elaslase | 22 | 828 | 333 | 214 |
| 229148 | RNELASIV | PANCNOT01 | Elaslase | 22 | 828 | 359 | 177 |
| 255224 | RNELASIV | PANCDIT01 | Elaslase | 22 | 828 | 424 | 358 |
| 255811 | RNELASIV | PANCDIT01 | Elaslase | 22 | 828 | 642 | 248 |
| 253038 | RNELASIV | PANCDIT01 | Elaslase | 22 | 828 | 643 | 320 |
| 227595 | RNELASIV | PANCNOT01 | Elaslase | 22 | 828 | 644 | 189 |
| 252594 | RNELASIV | PANCDIT01 | Elaslase | 22 | 828 | 644 | 278 |
| 254962 | RNELASIV | PANCDIT01 | Elaslase | 22 | 828 | 644 | 218 |
| 222569 | RNELASIV | PANCNOT01 | Elaslase | 22 | 828 | 646 | 200 |
| 251862 | RNELASIV | PANCDIT01 | Elaslase | 22 | 828 | 662 | 259 |
| 254930 | RNELASIV | PANCDIT01 | Elaslase | 22 | 828 | 689 | 245 |
| 224660 | RNELASIV | PANCNOT01 | Elaslase | 22 | 828 | 750 | 192 |
| 255041 | RNELASIV | PANCDIT01 | Elaslase | 22 | 828 | 752 | 212 |
| 225274 | RNELASIV | PANCNOT01 | Elaslase | 22 | 828 | 755 | 215 |
| 226611 | RNELASIV | PANCNOT01 | Elaslase | 22 | 828 | 758 | 186 |
| 251517 | RNELASIV | PANCDIT01 | Elaslase | 22 | 828 | 759 | 249 |
| 225072 | RNELASIV | PANCNOT01 | Elaslase | 22 | 828 | 763 | 195 |
| 251503 | RNELASIV | PANCDIT01 | Elaslase | 22 | 828 | 768 | 170 |

V Homology Searching of cDNA Clones and Deduced Proteins

Each sequence so obtained was compared to sequences in GenBank using a search algorithm developed by Applied Biosystems Inc. and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence compariotide and amino acid sequences to determine sequence similarity. Because of the local nature of the alignments, BLAST is especially useful in determining exact matches or in identifying homologues. Although it is ideal for matches which do not contain gaps, it is inappropriate for performing motif-style searching. The fundamental unit of BLAST algorithm output is the high-scoring segment pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output. An E greater than or equal to 25 usually indicates that a match is significant.

Figure 2A:
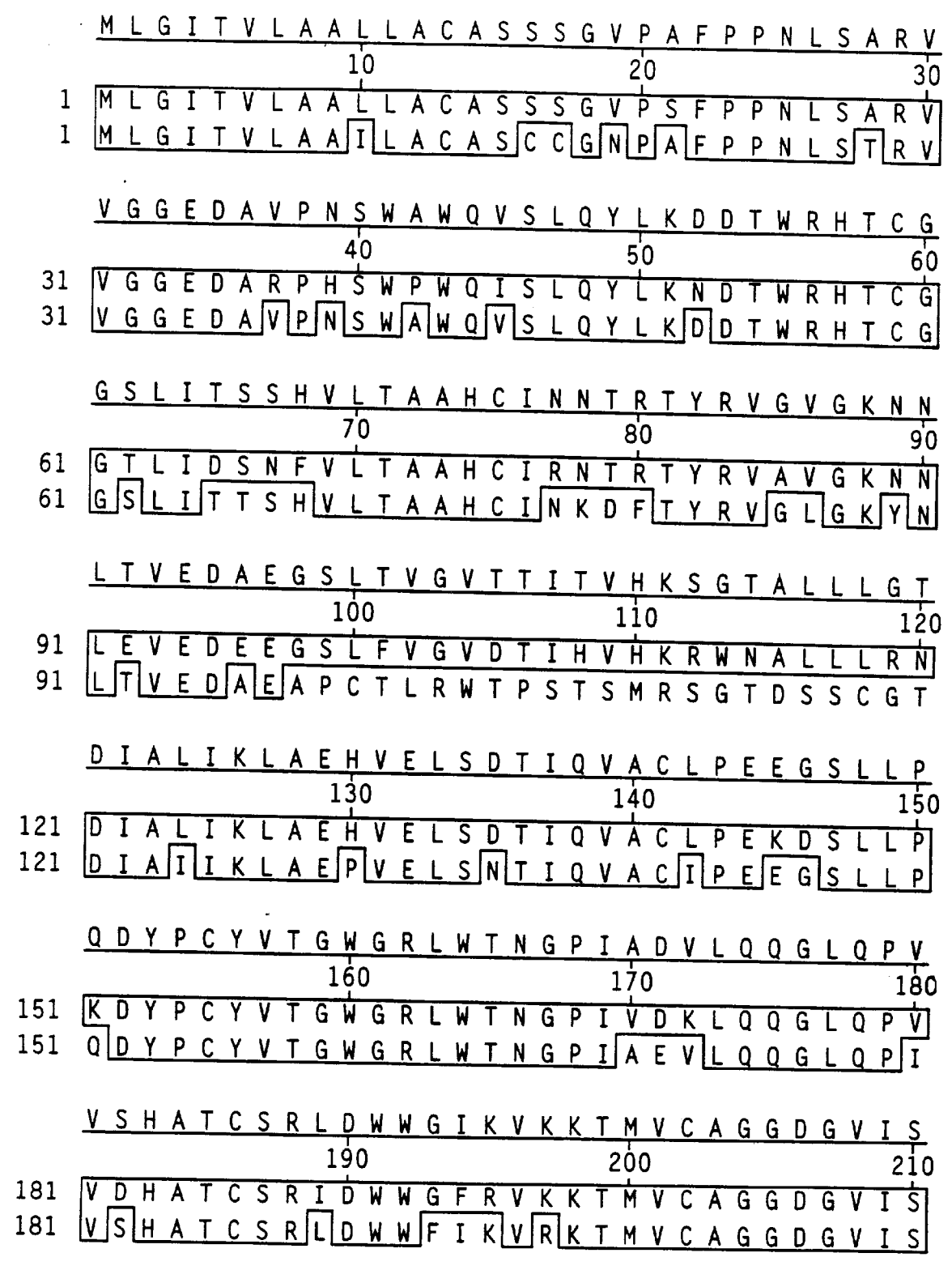
Figure 2B:
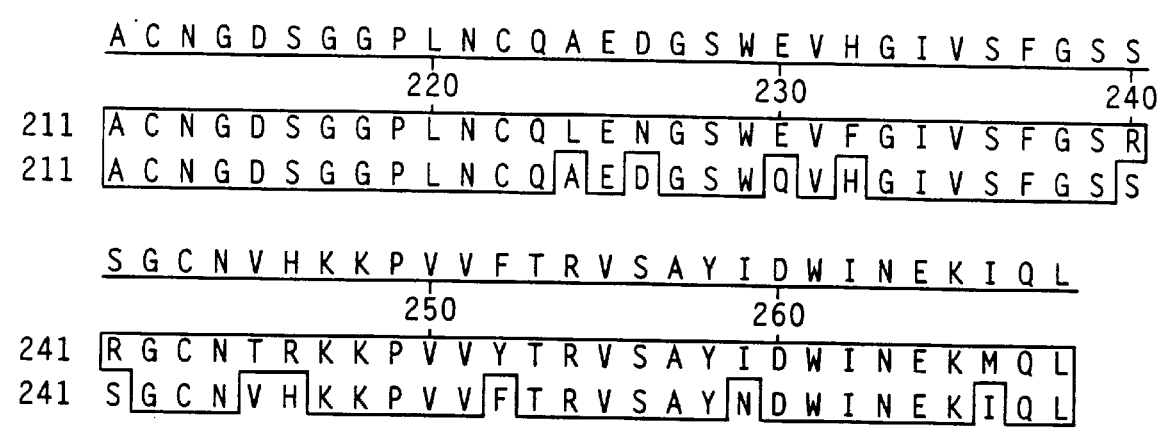

The sequence for the full length heIV gene was translated, and the putative in-frame translation is shown in FIG. 1. When all three possible predicted translations of the sequence were searched against protein databases such as SwissProt and PIR, no exact matches were found to the possible translations of HEIV. BLAST results showed that the polypeptide encoded by the full-length heIV coding sequence of the subject invention had an E parameter value of 142 when compared with the polypeptide sequence of the rat elastase IV gene (GenBank accession number 56091). FIG. 2 shows the comparison of the HEIV amino acid sequence with the rat elastase IV amino acid sequence. There is substantial homology among both molecules throughout most of their sequences. Of a sequence of 268 amino acids, HEIV shares about 72% homology with the rat elastase IV sequence. Additionally, the polynucleotide sequence of the present invention shares a lower degree of homology with a human elastase IIIA (about 63% homology).

VI Antisense Analysis

Knowledge of the cDNA sequence of the heIV gene will enable its use in antisense technology in the investigation of gene function. Oligonucleotides, genomic or cDNA fragments comprising the antisense strand of heIV can be used either in vitro or in vivo to inhibit expression of the protein. Such technology is now well known in the art, and probes can be designed at various locations along the nucleotide sequence. By transfection of cells or whole test animals with such antisense sequences, the gene of interest can effectively be turned off. Frequently, the function of the gene can be ascertained by observing behavior at the cellular, tissue or organismal level (e.g. changes in secretory pathways, lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of HEIV

Expression of HEIV may be accomplished by subcloning the cDNAs into appropriate expression vectors and transfecting the vectors into appropriate expression hosts. In this particular case, the cloning vector used in the generation of the full length clone also provides for direct expression of the included heIV sequence in E. coli. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The heIV cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as Saccharomyces cerevisiae, and bacteria such as E. coli. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced HEIV can be recovered from the conditioned medium and analyzed using chromatographic methods known in the art.

VIII Isolation of Recombinant HEIV

HEIV may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of a cleavable linker sequence such as Factor XA or enterokinase (Invitrogen) between the purification domain and the heIV sequence may be useful to facilitate expression of HEIV.

IX Production of HEIV Specific Antibodies

Two approaches are utilized to raise antibodies to HEIV, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of HEIV, as deduced from translation of the cDNA, is analyzed to determine regions of high immunogenicity. Oligopeptides comprising appropriate hydrophilic regions, antigenic regions, or regions likely localized to the surface of HEIV, as shown in FIG. 3, are synthesized and used in suitable immunization protocols to raise antibodies. Analysis to select appropriate epitopes is described by Ausubel F M et al., supra. The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; Ausubel F M et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled HEIV to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled HEIV, 1 mg/ml. Clones producing antibodies will bind a quantity of labeled HEIV which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8M^{-1}$, preferably $10^9$ to $10^{10}$ or stronger, will typically be made by standard procedures as described in Harlow and Lane (1988) *Antibodies: A Laboratory Manual*, Cold Spring Harbor Laboratory, Cold Spring Harbor, N.Y.; and in Goding (1986) *Monoclonal Antibodies: Principles and Practice*, Academic Press, New York City, both incorporated herein by reference.

These antibodies are particularly useful to control excessive elastase proteolytic activity contributing to tissue wasting, for example during acute pancreatitis.

X Diagnostic Test Using HEIV Specific Antibodies

Particular HEIV antibodies are useful for the diagnosis of conditions which are characterized by differences in the amount, and distribution of HEIV in human pancreas. Specifically, these conditions include those related to abnormal levels of tissue wasting. Diagnostic tests for HEIV include methods utilizing the antibody and a label to detect HEIV in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound HEIV, using either polyclonal or monoclonal antibodies specific for the respective protein are known in the art. Examples include enzyme-linked immunosorbent assay (ELISA), radioimmunoassay (RIA) and fluorescent activated cell sorting (FACS) . A two-site monoclonal-based immunoassay utilizing monoclonal antibodies reactive to two non-interfering epitopes on HEIV is preferred, but a competitive binding assay may be employed. These assays are described, among other places, in Maddox, Del. et al (1983) *J Exp Med* 158:1211.

XI Purification of Native HEIV Using Specific Antibodies

Native or recombinant HEIV can be purified by immunoaffinity chromatography using antibodies specific for HEIV. In general, an immunoaffinity column is constructed by covalently coupling the anti-HEIV antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of HEIV by preparing a fraction from cells containing HEIV in a soluble form. This preparation is derived by solubilization of the whole cell or of a subcellular fraction obtained via differential centrifugation by the addition of detergent or by other methods well known in the art. Alternatively, soluble HEIV containing a signal sequence may be secreted in useful quantity into the medium in which the cells are grown.

A soluble HEIV-containing preparation is passed over the immunoaffinity column, and the column is washed under conditions that allow the preferential absorbance of HEIV proteins. Then, the column is eluted under conditions that disrupt antibody/HEIV binding (e.g., a buffer of pH 2–3 or a high concentration of a chaotrope such as urea or thiocyanate ion), and HEIV is collected.

XII Drug Screening

This invention is particularly useful for screening compounds that inhibit elastolytic activity in pancreas tissue or other tissues. One method of compound screening utilizes eukaryotic or prokaryotic host cells which are stably transformed with recombinant nucleic acids expressing the HEIV polypeptide or a fragment thereof. Compounds are screened against such transformed cells by measuring, for example, alterations in HEIV activity by using specific substrates that will be hydrolyzed by HEIV.

Thus, the present invention provides methods of screening for test compounds which can affect HEIV activity. These methods comprise contacting such a compound with polypeptide and assaying for the presence of a complex between the compound and the polypeptide by methods well known in the art. After suitable incubation, free compound is separated from that in bound form, and the amount of bound compound is a measure of its ability to interfere in the regular functioning of HEIV.

Another technique for drug screening provides high throughput screening for compounds having suitable binding affinity to HEIV, and described in European Patent 84/03564, incorporated herein by reference.

This invention also contemplates the use of competitive drug screening assays in which neutralizing antibodies capable of binding HEIV specifically compete with a test compound for binding to HEIV. In this manner, the antibodies can be used to detect the presence of any peptide which shares one or more antigenic determinants with HEIV.

XIII Rational Drug Design

The goal of rational drug design is to produce structural analogs of biologically active polypeptides of interest or of small molecules with which they interact, including nonhydrolyzable analogs of GTP, etc. Any of these examples can be used to fashion drugs which are more active or stable forms of the polypeptide or which enhance or interfere with the function of a polypeptide in vivo (Hodgson J (1991) *Bio/Technolocy* 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous protease inhibitor-like molecules or to identify efficient inhibitors. Useful examples of rational drug design may include molecules which have improved activity or stability as shown by Braxton S and Wells J A (1992) *Biochemistry* 31:7796–7801 which act as inhibitors, or antagonists of native peptides as shown by Athauda S B et al (1993) *J Biochem* 113:742–746, incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the HEIV amino acid sequence provided herein will provide guidance to those employing computer modeling techniques in place of or in addition to x-ray crystallography.

XIV Use and Administration of Drugs

Since excessive HEIV production likely causes uncontrolled, nonspecific proteolytic activity, tissue wasting may result. Therefor, antibodies or inhibitors of HEIV, may be used to treat excessive wasting. A number of factors, such as endotoxins, exotoxins, viral infections, ischemia, anoxia and direct trauma, are believed to activate these proenzymes. The active enzymes then digest cellular membranes and cause edema, interstitial hemorrhage, vascular damage, coagulation necrosis, fat necrosis, and parenchymal cell necrosis. Both antibodies and inhibitors are termed therapeutic compounds.

Therapeutic compounds will be formulated in a nontoxic, inert, pharmaceutically acceptable aqueous carrier medium preferably at a pH of about 5 to 8, more preferably 6 to 8, although the pH may vary according to the characteristics of the formulation and its administration. Characteristics such as solubility of the molecule, half-life and antigenicity/immunogenicity will aid in defining an effective carrier. Recombinant, organic or synthetic molecules resulting from drug design may be equally effective in particular situations.

Therapeutic compounds may be delivered by known routes of administration including but not limited to topical creams and gels; transmucosal spray and aerosol, transdermal patch and bandage; injectable, intravenous and lavage formulations; and orally administered liquids and pills, particularly formulated to resist stomach acid and enzymes. The particular formulation, exact dosage, and route of administration will be determined by the attending physician and will vary according to each specific situation.

Such determinations are made by considering multiple variables such as the condition to be treated, the therapeutic compound to be administered, and the pharmacokinetic profile of the particular therapeutic compound. Additional factors which may be taken into account include disease state (e.g. severity) of the patient, age, weight, gender, diet, time of administration, drug combination, reaction sensitivities, and tolerance/response to therapy. Long acting therapeutic compound formulations might be administered every 3 to 4 days, every week, or once every two weeks depending on half-life and clearance rate of the particular therapeutic HEIV.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different uses of therapeutic compounds and that administration targeting a tissue or organ may necessitate delivery in a specific manner.

All publications and patents mentioned in the above specification are herein incorporated by reference. The foregoing written specification is considered to be sufficient to enable one skilled in the art to practice the invention. Indeed, various modifications of the above described modes for carrying out the invention which are readily apparent to those skilled in the field of molecular biology or related fields are intended to be within the scope of the following claims.

We claim:

1. A method for producing a polypeptide, said method comprising the steps of:
   a) culturing a host cell transformed with an expression vector comprising the polynucleotide encoding the polypeptide of SEQ ID NO:2 under conditions suitable for the expression of the polypeptide; and
   b) recovering the polypeptide from the host cell culture.

2. A purified polypeptide (HEIV) having the amino acid sequence of SEQ ID NO:2.

3. A diagnostic composition comprising the polypeptide of claim 2.

4. A composition comprising the polypeptide of claim 2 and a pharmaceutically acceptable excipient.

5. A method of screening a plurality of compounds for specific binding affinity with the polypeptide of claim 2 comprising the steps of:
   a) providing a plurality of compounds;
   b) combining HEIV with each of a plurality of compounds for a time sufficient to allow binding under suitable conditions; and
   c) detecting binding of HEIV to each of the plurality of compounds, thereby identifying the compounds which specifically bind HEIV.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 959 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: HUMAN ELASTASE HOMOLOG
        ( B ) CLONE: 226990

( x i ) SEQUENCE DESCRIPTION: SEQ ID NO:1:

| | | | | | |
|---|---|---|---|---|---|
| AATAGACAAT | TCGGCACGAG | CATGTTGGGC | ATCACTGTCC | TCGCTGCGCT | CTTGGCCTGT | 60 |
| GCCTCCAGCA | GTGGGGTGCC | CAGCTTCCCG | CCCAACCTAT | CCGCCCGAGT | GGTGGGAGGA | 120 |
| GAGGATGCCC | GGCCCCACAG | CTGGCCCTGG | CAGATCTCCC | TCCAGTACCT | CAAGAACGAC | 180 |
| ACGTGGAGGC | ATACGTGTGG | CGGGACTTTG | ATTGATAGCA | ACTTCGTCCT | CACTGCCGCC | 240 |
| CACTGTATCA | GAAACACCCG | GACCTACCGT | GTGGCCGTGG | GAAAGAACAA | CCTGGAGGTG | 300 |
| GAAGACGAAG | AAGGATCCCT | GTTTGTGGGT | GTGGACACCA | TCCACGTCCA | CAAGAGATGG | 360 |
| AATGCCCTCC | TGTTGCGCAA | TGATATTGCC | CTCATCAAGC | TTGCAGAGCA | TGTGGAGCTG | 420 |
| AGTGACACCA | TCCAGGTGGC | CTGCCTGCCA | GAGAAGGACT | CCCTGCTCCC | CAAGGACTAC | 480 |
| CCCTGCTATG | TCACCGGGTG | GGGCCGCCTC | TGGACCAACG | GCCCCATTGT | TGATAAGCTG | 540 |
| CAGCAGGGCC | TGCAGCCCGT | GGTGGATCAC | GCCACGTGCT | CCAGGATTGA | CTGGTGGGGC | 600 |
| TTCAGGGTGA | AGAAAACCAT | GGTGTGCGCT | GGGGGCGATG | GCGTCATCTC | AGCCTGCAAT | 660 |
| GGGGACTCCG | GTGGCCCACT | GAACTGCCAG | TTGGAGAACG | GTTCCTGGGA | GGTGTTTGGC | 720 |
| ATCGTCAGCT | TTGGCTCCCG | GCGGGGTTGC | AACACCCGCA | AGAAGCCGGT | AGTCTACACC | 780 |
| CGGGTGTCCG | CCTACATCGA | CTGGATCAAC | GAGAAAATGC | AGCTGTGATT | TGTTGCTGGG | 840 |
| AGCGGCGGCA | GCGAGTCCCT | GAAACAGAAA | TAAACTTCCT | TCTCCTCGGG | GTCGTAAACA | 900 |
| GAGGATTCGG | TTAACTTAGG | GTAAATACCT | GGTGGATCGT | CAGGGACGGG | CGGGGCTTA | 959 |

( 2 ) INFORMATION FOR SEQ ID NO:2:

( i ) SEQUENCE CHARACTERISTICS:
        ( A ) LENGTH: 268 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Leu | Gly | Ile | Thr | Val | Leu | Ala | Ala | Leu | Leu | Ala | Cys | Ala | Ser | Ser |
|---|---|---|---|---|---|---|---|---|---|---|---|---|---|---|---|
| 1 | | | | 5 | | | | | 10 | | | | | 15 | |
| Ser | Gly | Val | Pro | Ser | Phe | Pro | Pro | Asn | Leu | Ser | Ala | Arg | Val | Val | Gly |
| | | | 20 | | | | | 25 | | | | | 30 | | |
| Gly | Glu | Asp | Ala | Arg | Pro | His | Ser | Trp | Pro | Trp | Gln | Ile | Ser | Leu | Gln |

|  |  |  | 35 |  |  | 40 |  |  |  | 45 |  |  |  |  |
|---|---|---|---|---|---|---|---|---|---|---|---|---|---|---|
| Tyr | Leu 50 | Lys | Asn | Asp | Thr | Trp 55 | Arg | His | Thr | Cys | Gly 60 | Gly | Thr | Leu | Ile |
| Asp 65 | Ser | Asn | Phe | Val | Leu 70 | Thr | Ala | Ala | His | Cys 75 | Ile | Arg | Asn | Thr | Arg 80 |
| Thr | Tyr | Arg | Val | Ala 85 | Val | Gly | Lys | Asn | Asn 90 | Leu | Glu | Val | Glu | Asp 95 | Glu |
| Glu | Gly | Ser | Leu 100 | Phe | Val | Gly | Val | Asp 105 | Thr | Ile | His | Val | His 110 | Lys | Arg |
| Trp | Asn | Ala 115 | Leu | Leu | Leu | Arg | Asn 120 | Asp | Ile | Ala | Leu | Ile 125 | Lys | Leu | Ala |
| Glu | His 130 | Val | Glu | Leu | Ser | Asp 135 | Thr | Ile | Gln | Val | Ala 140 | Cys | Leu | Pro | Glu |
| Lys 145 | Asp | Ser | Leu | Leu | Pro 150 | Lys | Asp | Tyr | Pro | Cys 155 | Tyr | Val | Thr | Gly | Trp 160 |
| Gly | Arg | Leu | Trp | Thr 165 | Asn | Gly | Pro | Ile | Val 170 | Asp | Lys | Leu | Gln | Gln 175 | Gly |
| Leu | Gln | Pro | Val 180 | Val | Asp | His | Ala | Thr 185 | Cys | Ser | Arg | Ile | Asp 190 | Trp | Trp |
| Gly | Phe | Arg 195 | Val | Lys | Lys | Thr | Met 200 | Val | Cys | Ala | Gly | Gly 205 | Asp | Gly | Val |
| Ile | Ser 210 | Ala | Cys | Asn | Gly | Asp 215 | Ser | Gly | Gly | Pro | Leu 220 | Asn | Cys | Gln | Leu |
| Glu 225 | Asn | Gly | Ser | Trp | Glu 230 | Val | Phe | Gly | Ile | Val 235 | Ser | Phe | Gly | Ser | Arg 240 |
| Arg | Gly | Cys | Asn | Thr 245 | Arg | Lys | Lys | Pro | Val 250 | Val | Tyr | Thr | Arg | Val 255 | Ser |
| Ala | Tyr | Ile | Asp 260 | Trp | Ile | Asn | Glu | Lys 265 | Met | Gln | Leu |  |  |  |  |